United States Patent [19]

Amotz et al.

[11] 3,980,521

[45] Sept. 14, 1976

[54] IMMOBILIZATION OF GLUCOSE ISOMERASE

[75] Inventors: Shmuel Amotz, Malev; Tage Kjaer Nielsen, Herlev; Niels Otto Thiesen, Lyngby, all of Denmark

[73] Assignee: Novo Industri A/S, Bagsvaerd, Denmark

[22] Filed: Aug. 28, 1974

[21] Appl. No.: 501,292

[52] U.S. Cl. .............................. 195/68; 195/31 F; 195/59; 195/63; 195/65; 195/DIG. 11
[51] Int. Cl.² ..................... C07G 7/02; C12K 1/00
[58] Field of Search ....... 195/31 F, 63, 68, DIG. 11, 195/59, 65, 52

[56] References Cited
UNITED STATES PATENTS

| | | | |
|---|---|---|---|
| 3,753,858 | 8/1973 | Takasaki et al. | 195/31 F |
| 3,779,869 | 12/1973 | Zienty | 195/68 |
| 3,821,086 | 6/1974 | Lee et al. | 195/31 F |
| 3,843,442 | 10/1974 | Moskowitz | 195/31 F |

FOREIGN PATENTS OR APPLICATIONS 2,107,801   1972   France

OTHER PUBLICATIONS

Avrameas et al., The Cross-Linking of Proteins With Glutaraldehyde and Its Use For the Preparation of Immuno–adsorbents, Immunochemistry, vol. 6, 1969 (pp. 53–66).

*Primary Examiner*—David M. Naff
*Attorney, Agent, or Firm*—Fidelman, Wolffe & Waldron

[57] ABSTRACT

A water insoluble glucose isomerase product is prepared from microorganism cells exhibiting glucose isomerase activity by concentrating and homogenizing the microorganism cells to form a homogenized cell concentrate containing ruptured cells, reacting the homogenized concentrate with glutaraldehyde to form a coherent solid product and removing water and shaping the coherent product into a divided form.

11 Claims, 1 Drawing Figure

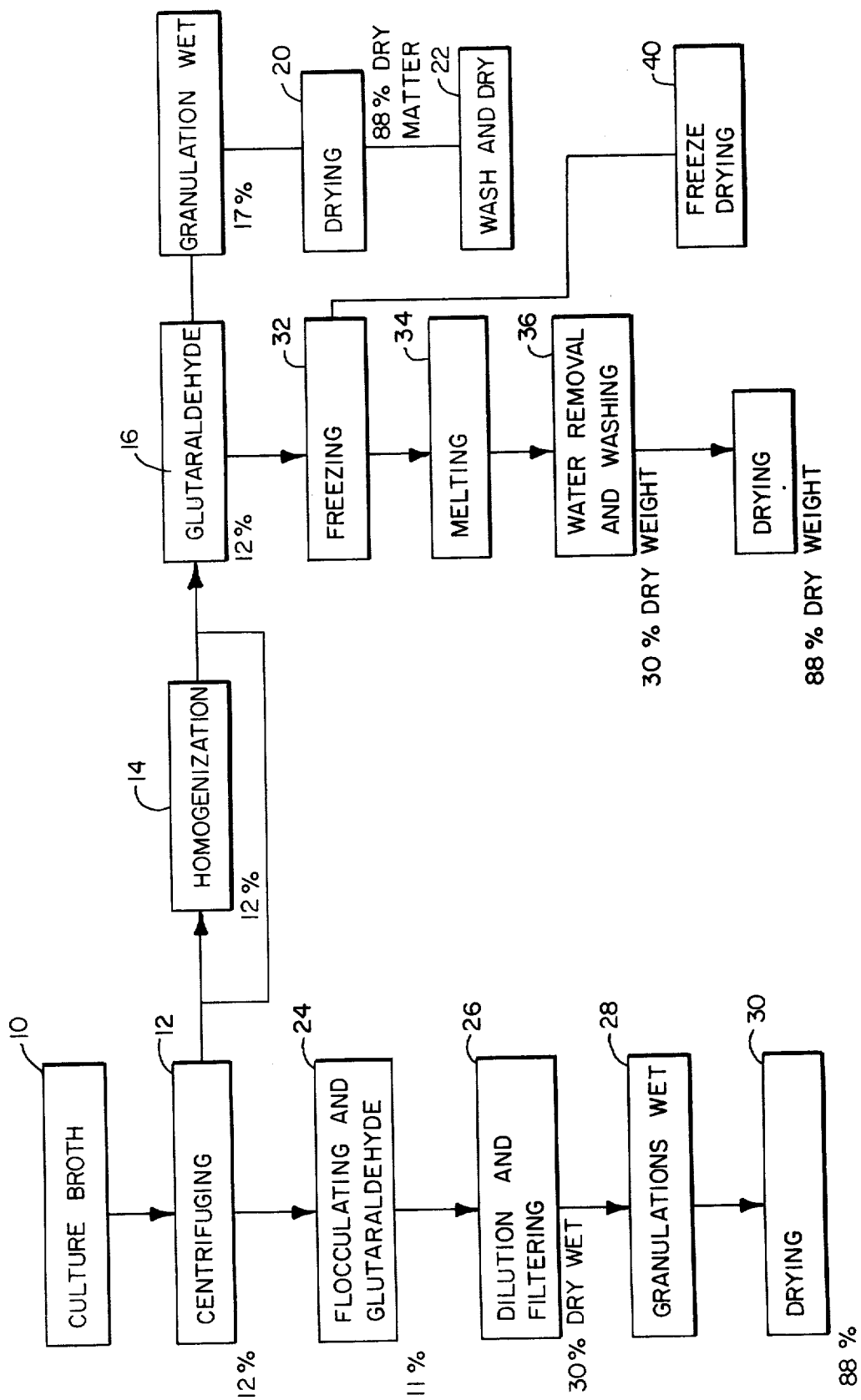

IMMOBILIZATION OF GLUCOSE ISOMERASE

BACKGROUND OF THE INVENTION

The art has long appreciated that one time use of enzymes to conduct a desired enzymatic reaction may involve such an inordinate enzyme cost as to make conduct of the reaction prohibitively expensive.

In particular, it is known that glucose can be isomerized enzymatically to a much sweeter, about 50—50 mixture of glucose and fructose, but the enzyme expense is great and the isomerization procedure must be tailored to match the characteristics of the enzyme. Since a reusable enzyme offers hope for a low cost process, the possibility for multiple reuse of enzymes has not escaped the attention of the art. Numberous proposals have been made to stabilize and/or alternatively, to immobilize both cellular and cell free glucose isomerase enzymes.

Since enzyme reuse requires recovery of the enzyme from the reaction mixture, soluble enzymes are insolubilized and attached to a matrix of some sort. In the instance of glucose isomerase, an intracellular enzyme, the enzyme is already bonded to or entrapped inside the microbial cell, but leaching out of the enzyme and/or disintegration of the cell must be avoided. Also, microbial cells are quite tiny. Larger particles would be more desirable.

A related point of some significance to isomerization of glucose is the desirability of being certain that reagents employed to stabilize or encapsulate the glucose isomerase containing cells will not release materials that constitute a detriment to the final glucose/fructose syrup. Some of the immobilization techniques suggested to the art may never be employed in commercial practice because reagents and reaction products have not been accepted as non-toxic. In this regard, reaction of microbial cells with glutaraldehyde offers an advantage since glutaraldehyde reaction products are generally recognized as ingestible (certainly in the miniscule quantities that might appear in the syrup product).

In this connection, reference is made to U.S. Pat. No. 3,779,869 as being directed to stabilization of glucose isomerase containing bacterial cells by reaction with glutaraldehyde. Other suggestions have been made to the art to cross-link various enzymes by a reaction with glutaraldehyde.

Glutaraldehyde is known to react with (amino) nitrogen containing materials, even enzymes. However, whole cells of glucose isomerase microorganisms are simply not reactive enough with glutaraldehyde to cross-link into multi-cell particles. Suggestions for cross-linking, insolubilization and immobilization of enzymes have involved inclusion of an extraneous reactant with glutaraldehyde ingredient (such as for example albumin) for covalent bonding of enzymes thereto. Reference is made to British Pat. No. 1,257,263 for detailed description of such (and other like) expedients. Unfortunately, addition of extraneous reactant, in the needed quantities significantly dilutes the glucose isomerase, lowering the unit activity of the product proportionate to the dilution. Higher unit activity immobilized products can, of course, be prepared if the glucose isomerase is removed from the cell and purified prior to immobilization. However, the processing costs and activity loss incident to processing sharply increase the expense of any high activity product.

The situation is particularly troublesome in the instance of glucose isomerase. Isomerization of glucose on an industrial scale requires very large quantities of a relatively low cost enzyme product with the highest possible unit activity. Stabilized cells would seem best suited to this requirement, but providing for use, recovery and reuse of individual cells on an industrial scale is an engineering nightmare. If a significant reuse factor, e.g. five or more times, can be attained, the art is willing to accept the somewhat lowered unit activity inherent in a particulate product (far larger than microorganism cells).

It has now been discovered that a controlled particle size glucose isomerase product can be prepared without diluting the enzyme content by inclusion of an extraneous immobilization reactant. It has been ascertained that the cells themselves contain more than enough nitrogenous (and perhaps other) constituents reactive with glutaraldehyde to create a gel product. Such constituents must first be liberated from the microorganism cells, but when liberated will serve the purpose without need for intermediate purification.

Liberation of nitrogenous constituents such as for example proteins and nucleic acids can be effected by mechanical action or autolysis. The liberation need not be complete. Fracturing as little as 25% of the cells can release sufficient reactants to allow creation of a gel product.

SUMMARY OF THE INVENTION

The process of the present invention involves treatment of a bacterial cell concentrate, wherein not more than about 75% of the cells are intact cells, with glutaraldehyde to convert the cells into a tough, dimensionally stable, controlled particle size enzyme product. The ruptured cells provide sufficient material reactive with glutaraldehyde to convert the concentrate into a coherent reaction product, which for example may be a gel.

The coherent reaction product is dewatered, e.g. by drying, and shaped into a suitable size subdivided form exceeding (by far) 10 microns in size.

DESCRIPTION OF THE INVENTION

The particular microorganism source of the glucose isomerase forms no part of the present invention. Many microorganisms have been identified as exhibiting glucose isomerase activity. A large body of literature and patents relate to sources of this enzyme. However, most, perhaps all of the microorganism sources of glucose isomerase already known produce the enzyme intracellularly. Be that as it may, only intracellular sources of glucose isomerase are of interest for practice of the present invention.

The bacterial cells may be cultivated according to procedures known to the art (preferably those most suitable for production of a high glucose isomerase activity cell). The cells are appropriately separated from the fermentation broth by filtration, centrifugation, etc., to form a concentrate containing from 3–30% weight by volume dry matter therein. In terms of the present invention, the presence of autolysed and disrupted cells and even free enzyme in the cell concentrate is crucial, therefore permitting concentration of the microbial cells by large scale commercial equipment such as self-cleaning sludge centrifuges. Relatively harsh handling conditions, even autolysis due to processing delays are acceptable.

Indeed if a substantial degree of cell rupture, autolysis, etc. does not occur during the course of recovery and concentration, then rupture is deliberately caused to the point where the concentrate contains not more than about 75%, preferably less than 60% whole cells. Complete or 100% rupture of the cells is contemplated for practice of this invention.

Reaction with glutaraldehyde is carried out in an aqueous suspension of fragmented cells and likely some of the liberated cellular constituents, including glucose isomerase itself are in solution. Accordingly, cell disruption or fracturing should be carried out only after the cells have been concentrated beyond their usual (dilute) content in the fermentation medium. In practical terms this means that the microorganism is separated from its growth medium, e.g. centrifuged off, as a bacterial cell concentrate containing from 3 to about 20% dry matter. Then as incident to the concentration, or subsequent thereto, the desired disruption of the cells is carried out, as for example by autolysis or by homogenization.

The cell concentrate being immobilized and crosslinked by reaction with glutaraldehyde has then from 0–75% whole cells and a dry matter content of 3–30% by weight. Whatever glucose isomerase has been liberated in soluble form remains in the concentrate to become incorporated into the enzyme product.

Within the context of this invention dry matter is the residue left behind by drying at 105°C. for 16 hours. Drying 24 hours at 60°C. under vacuum will give an alternative dry matter content measurement.

The quantity of glutaraldehyde reacted with cell concentrate is important, although the wide proportion of from 1–100% by weight of glutaraldehyde based upon dry matter content is contemplated. The amount of glutaraldehyde used is important. Too little would make the product unsuitable for industrial use and too much would tend to reduce unit activity of the final enzyme product. The convenient range of ratios of the dry weight of the glutaraldehyde to the dry matter in the starting material is found to be from about 0.01 to about 1, preferably from about 0.04 to about 0.4 and in particular from about 0.05 to about 0.3. The relative proportion of glutaraldehyde to be employed may well vary from microorganism to microorganism, even require tailoring to fit different industrial scale glucose conversion installations.

The glutaraldehyde may be added in the form of commercially concentrated (e.g. 25%) glutaraldehyde solution to the cell concentrate and the mixture stirred thoroughly to assure an even dispersion of the glutaraldehyde.

The cross-linking reaction and product recovery procedure of the present invention is capable of wide variations.

In one preferred embodiment the starting material is either a concentrated fermentation broth or a homogenized concentrate and the glutaraldehyde is added in such an amount and the temperature range is so chosen so as to enable the mixture to gel within one hour.

In another preferred embodiment the starting material which may be either a concentrate or a homogenate is treated with a flocculent before the addition of glutaraldehyde so as to form aggregates and enhance the cross-linking reaction.

In another preferred embodiment the cross-linking mixture is frozen so as to form an inhomogeneous gel which leads to a more porous product. As a starting material any form of enzyme can be used and the conditions for the cross-linking step need not be so chosen so as to allow gelling prior to freezing. After freezing the gel is thawed at a temperature above the freezing point. This allows the cross-linking reaction to continue and form the porous product. The conditions before the freezing step can be so chosen so as to allow either a very limited or a fairly extensive cross-linking. In the first case the product is more flaky while in the latter case the product is more spongy.

Accordingly, practice of this invention involves numerous alternatives, reference being made to the attached flow sheet for a graphic representation of how the basic process can be varied to result in different product modes of the invention.

Referring now to the drawing it may be seen that the cell culture broth 10 is always concentrated suitably by centrifuging 12 to 12% dry matter desirably under conditions which cause the desired substantial degree of cell rupture. In one variation the cells may be subject to complete homogenation 14 to a 100% cell ruptured state. As has already been pointed out, rupture of the cells frees components thereof reactive with glutaraldehyde.

In one preferred treatment mode the homogenate or the concentrate is treated 16 with glutaraldehyde, e.g. with 40% by weight glutaraldehyde, and the mixture allowed to remain quiescent at ambient temperature until the entire mass has gelled. While the gel is still soft (somewhat like custard or green cheese) it is granulated 18 and optionally washed. Thereafter the gel is dried 20, desirably at only mildly elevated temperatures, e.g. 30°–50°C. to for example 88% dry matter. The product may then be washed and re-dried 22. The granular high activity products which result constitute one preferred product mode of this invention.

The hardness of the granular product can be controlled by adjustment of the initial quantity of glutaraldehyde reactant and, or alternatively by the degree of washing carried out as an incident of the wet granulation. Washing removes unreacted glutaraldehyde and results in a slightly softer product. Apparently, the reactions continue, hardening the product as it dries. The last washing step 22, is intended principally to remove the very fine particles.

The dry particles of product have exceptional dimensional stability and structural strength, while retaining a high proportion of the original enzyme activity present in the microbial cells. The particulate glucose isomerase product of this invention is capable of multiple reuse conversion of glucose to fructose in batch or column reactors.

Processing advantages are offered by an alternative treatment sequence wherein the cell concentrate is treated with a flocculent to agglomerate the cells, then reacted with glutaraldehyde 24. After gelation the gel is washed and filtered to remove some water, flocculant, unreacted glutaraldehyde, whatever. At this stage the dry matter content of the gelled mass has been increased from for example 11% to 30%. Thereafter the filter cake is granulated 28 and dried 30, e.g. to 88% dry matter. High enzyme activity tough particles result. A principal advantage of flocculating the cell concentrate is that a more dewaterable gel results, reducing the load on the drier equipment.

Both processing and product advantages are offered by an alternative treatment sequence which includes freezing 32 the glutaraldehyde treated cell concentrate.

The freezing can be carried out after gelation or prior thereto, immediately after admixing concentrate and glutaraldehyde in which event the reaction becomes complete upon melting 34. In either event syneresis occurs. Water washing and water removal leave behind a somewhat concentrated in dry matter product, e.g. 30%. Thereafter the product is dried, e.g. to 88% dry matter. The freezing produces a laminar or flakey product which is somewhat resilient, fibrous and/or almost spongy in nature. As compared to the granular products, the freeze mode product is almost free of excessively fine particles. A greater recovery of the total enzyme activity is believed to occur with the freeze process variation, and presence of a freeze step is preferred for the overall process of this invention.

Still another mode of the invention involves freeze drying 40 the frozen reaction product. However, freeze drying involves expensive vacuum equipment, and relatively high costs of operation.

Since any mode of evaporative drying involves processing expenses, the dewatering facilitated by the freezing and flocculating modes offer some advantages. As noted in the flow sheet, the cross-linked washed product can be pressed (on a filter) to remove some of the original water content leaving at least about a 30% dry matter product. If desired, such product can be employed for glucose isomerization. However, some drying is preferred and the preferred product contains at least about 80% dry matter.

The microorganism source of the glucose isomerase employed for practice of this invention is not believed to be critical. However, a preferred source of glucose isomerase is *B. coagulans*, a known producer of this enzyme. Particularly preferred is the atypical *B. coagulans* described in copending application Ser. No. 428,682, filed Dec. 27, 1973. This microorganism ruptures readily, releasing both the enzyme in soluble form and reactive constituents such as proteins, nucleic acids, etc. Indeed, if desired, the cell debris may be removed from a homogenized concentrate so that a soluble enzyme and soluble reactive cell constituents dissolved in the filtrate or centrifugate may be reacted to form the cross-linked product.

Typical exemplary strains are NRRL B-5649-5666 and B-5351.

For further understanding of the practice of the present invention, reference is made to the following specific examples thereof.

EXAMPLE 1

Preparation of a concentrate and its immobilization.

Isomerase containing cells of bacillus species NRRLB 5656 are cultivated, then the cells are recovered from the fermentation broth by centrifugation on a Westfalia SAMS with a self-cleaning bowl, and the pH adjusted to 6.3. The concentrate is estimated to contain approximately 10% dry matter, and about 40% intact cells.

To 1 kg of the concentrate, 38 ml of commercial 50% glutaraldehyde was added with sufficient stirring to thoroughly intermix glutaraldehyde and cell concentrate. Thereafter the reaction mass was left at ambient in a quiescent state.

After an hour, the reaction mixture had gelled into a coherent mass approximately the consistency of cheese curd. The mass was broken up by mild stirring, and washed with two volumes of deionized water, and the water drained away.

The gel pieces were then transferred to a vacuum drum-dryer where the approximately 1 kg weight was dehydrated at 50°C. to a weight of about 160 grams. During the course of dehydration, the soft gel pieces became converted into a tough, dimensionally stable material. The dehydrated pieces were further comminuted into particles less than 1 mm diameter. The enzyme recovery will vary batch to batch from 50–60% of the initial activity. However, about 15% by weight of the product constitutes excessively fine material (of 1–70 microns).

EXAMPLE II

Immobilization with freezing.

The procedure of Example 1 was followed up to the preparation of the glutaraldehyde cell concentrate mixture and quiescent standing preparation of a gelled mass.

Thereafter the gel (in its container) was transferred to a deep freeze and left overnight. The next day the frozen gel was thawed to ambient temperature, resulting in a watery mass. More water was added with stirring then the water drained off. The product was then dried in the rotary drier to a weight of about 160 grams.

The ultimate product consisted of spongy particles, somewhat flakey in appearance. The recovery of apparent activity varied batch to batch between 60–70%. However, virtually no fines are produced.

EXAMPLE III

Immobilization with a flocculant.

1550 l of a culture broth from a fermentation of glucose isomerase producing Bacillus coagulans NRRL B 5656 were concentrated by centrifuging it at 10°C. to give a sludge containing about 12 g dry weight (105°C.) per 100 ml of concentrate.

11 kg of this concentrate (pH 7.9) was left at 20°C. for 3 hours at room temperature with a mild stirring in order to let the Bacillus Coagulans cells autolyse. The pH was adjusted to 6.5 with diluted acetic acid. To the sludge containing more than 70% of the activity in a soluble form 330 ml of a 50% glutaraldehyde solution was added to give a concentration of about 1.4% of glutaraldehyde w/v in the reaction mixture. After one hour the partly cross-linked gel was agitated vigorously after addition of 20 l of deionized water. To the suspension was added 80 ml of a 30% solution of Drewfloc EC 25 to make a clear solution. The suspension was filtered to remove as much water as possible. The filtercake was dried in vacuum at 35°C. The dried cake was ground to a particle size of less than 300 $\mu$. The activity was determined by isomerization in batch with a spray-dried powder made from the concentrate as a reference. The conditions were: pH = 7.0, 65°C., 0.1 g $CoSo_4 \cdot 7H_2O/l$ and 2.0 g $Mg So_4 \cdot 7H_2O/l$, 40 % glucose w/v. The feed was flushed with nitrogen. The apparent activity of the immobilized enzyme was over 70% of the reference. After use the immobilized enzyme was removed by filtration and reused. This was done five times. After five successive uses the activity had not shown a significant drop.

A second portion of the autolyzed cell concentrate was treated with 20 ml of 30% Drewfloc EC 25 per kg of sludge before the reaction with 1.4% w/v glutaraldehyde. Essentially the same product resulted.

EXAMPLE IV

Homogenate (flocculated and cross-linked).

12 l of sludge as described in Example 3 was homogenized in order to create free enzyme by disruption of the cells. At a pH of about 7.5 it was pumped through a Manton Caulin homogenizer type SP 15M-8TA with a single stage homogenizing valve assembly. The pressure drop was 300–350 kg/cm$_2$. The homogenate which contained practically all the activity in a soluble form was flocculated with 30 ml/l of a 50% w/w Drewfloc EC 25 solution and reacted with 40 ml/l solution of a 50% w/w glutaraldehyde to give a concentration of about 2.0% w/w of glutaraldehyde in the solution. After a reaction time of one hour the gel formed was broken up mechanically, diluted with 20 l of deionized water and further processed according to Example 1.

EXAMPLE V

Flocculant added to a homogenate after the glutaraldehyde.

The sludge (as described in Example 3) was homogenized under the conditions used in Example 4. To the sludge at a pH of 7.7 and 25°C. was added 50% w/w glutaraldehyde solution to give a concentration of 2.0% w/w in the solution. After one hour reaction time the gel was broken up mechanically, diluted with 1 volume of water. 50 ml of a 30% w/w Drewfloc EC 25 was added to give a clear water phase in the suspension. The mixture was filtered. The filtercake was ventilated with compressed air to remove some of the free water. The filtercake was granulated by means of an oscillatory granulater equipped with an ASTM 18 mesh screen and dried in a fluid bed with an inlet air temperature of 50°C.

The preparation and gel recovery procedure was repeated, except that the reaction with glutaraldehyde was carried out at a temperature of 8°–10°C. The filtercake was extruded on an axial extruder equipped with a screen with 0.8 mm holes. The product was dried in vacuum at 35°C. 300 g was loaded in a jacketed column of 1 l and at a temperature of 60°C. and at a pH of 7.2 a 40% w/w' solution of glucose was pumped through the column at a speed of 1 l/hour. The conversion was 43%. The said glucose solution contained per liter 0.1 g $CoSo_4.7H_2O$ and 2.0 g $MgSo_4.7H_2O$.

EXAMPLE VI

Preparation of a concentrate of a fermentation broth and its immobilization.

(100 l of) broth from a fermentation of a glucose isomerase containing *B. coagulans* NRRL B 5656 were concentrated by centrifuging it at 10°C., to give 12 g dry weight per 100 ml concentrate.

20 l of the said concentrate were treated with a buffered 20% w/v acetic acid having a pH 3.5 to lower the concentrate's pH to 6.3. Then 800 ml of 50% w/w glutaraldehyde solution was added, the mixture thoroughly agitated, then left at 20°C. for 45' to gel. The gel thus formed was dispersed in 40 l deionized water, filtered on a filter press, and the cake ventilated in the filter press to remove some of the water, and the partially dried cake (11.6 kg) was granulated in an oscillatory granulator with a No. 18 mesh and dried in drying oven at 35°C. to give 2.3 kg of very tough particles, which retained their physical properties even after being agitated in water at 60°C. for a few days.

A sample of the granules containing 88–300 $\mu$ particles was then agitated for 20 hours at 65°C. in a medium consisting of 40% w/w/ glucose, 0.1% w/v $MgSO_4.7H_2O$, 0.01% w/v $CoSo_4.7H_2O$, at pH 6.6, to give 63% of the apparent activity of the spray dried powder of the original concentrate tested under identifical conditions.

A cross-linked filter cake prepared as above was extruded by means of an axial extruded with a screen of 0.7 mm, dried in a fluidized bed at an inlet air temperature of 60°C., to give particles of cylindrical shape with very narrow size distribution. When tested as above, they showed 52% recovery of apparent activity.

Cell concentrate was treated with 0.8% glutaraldehyde at pH 6.3 and poured into trays which were left in a drying oven with circulating air at 50°C. The resulting cakes were ground in a mortar and tested as above to show 48% recovery of the apparent activity.

10 l of the cell concentrate was homogenized by means of a Manton-Goulin homogenizer at 400 atm. to give a homogenate with about 95% of the activity in a soluble form.

Granules prepared from the homogenate and tested as above showed 71% recovery of apparent activity, and had good physical properties.

100 ml of the homogenate was stirred 20 minutes with 5 ml 20% w/w glutaraldehyde pH 6.8, spread on a surface as a 1 cm layer, dried at 20°C., and ground in a mortar to give 11.6 g particles. These were stirred 20' in 200 ml deionized $H_2O$ and dried to give 9.7 g tough particles.

The particles were loaded in a jacketed column maintained at 60°C., and feed consisting of 40% w/w glucose and 0.1% w/v $MgSO_4.7H_2O$ pH 7.8 was started at 45 ml/hour. After 44 hours the conversion was found to be 45.2%.

EXAMPLE VII

Concentrate, freezing.

100 l of broth from a fermentation of a glucose isomerase containing *B. coagulans* were concentrated by centrifuging it at 10°C., to give 12 g dry weight per 100 ml concentrate.

10 l of concentrate were cooled down to 5°C., mixed thoroughly with 300 ml 50% w/w glutaraldehyde, poured on a tray and placed at −20°C. to freeze. After the freezing was complete, it was thawed at 20°C., and the gel thus formed was dispersed in 20 l deionized water, filtered, pressed on the filter to remove as much liquid as possible, granulated in an oscillatory granulator with a 7 mesh screen, and dried in a vacuum drum dryer, to give fibrous porous granules.

A sample of the granules containing 88–300 $\mu$ particles was then agitated for 20 hours at 65°C. in a medium consisting of 40% w/w glucose, 0.2% w/v $MgSO_4.7H_2O$, 0.01% w/v $CoSo_4.7H_2O$, at pH 6.6, to give 79% of the apparent activity of the spray dried powder of the original concentrate tested under identical conditions.

Granules prepared as above, except that the drying step was omitted, were less hard but fairly tough. They showed 81% recovery of the apparent activity.

EXAMPLE VIII

Different enzyme concentrations.

3 portions 100 ml of the homogenate of Example 6 were treated in the following way:
a. mixed with 10 ml 20% w/w glutaraldehyde pH 6.8
b. same, only first diluted with 100 deionized $H_2O$
c. same, only first diluted with 200 deionized $H_2O$ All were frozen, thawed at 20°C., the gels formed dispersed in 300 ml deionized $H_2O$, filtered, dried at 20°C., and granulated. When 5 g of each were then tested at 30 ml/hour of 40% glucose w/w solution after 20 hours, they showed the following results:

|     | % conversion |
| --- | --- |
| (a) | 46.4 |
| (b) | 45.8 |
| (c) | 47.4 |

EXAMPLE IX

Comparison between different degrees of cell disruption.

A concentrate (60% disruption) and a homogenate (95% disruption) were prepared as in Example 6.

200 ml of each were then mixed for 20' with 8 ml 50% w/w glutaraldehyde, frozen, thawed at 20°C., and the gel thus formed were squeezed, broken up, agitated 20' in 1 liter deionized water, filtered, pressed on the filter, redispersed in 1 liter deionized water, refiltered, dried at 20°C., and granulated. 5 g of each were tested in columns as in Example 6 at 30 ml/hour, to show the following performance after 20 hours:

|     | % conversion |
| --- | --- |
| concentrate | 40.0 |
| homogenate | 45.1 |

When checked for rigidity after the run, the concentrate particles were found to be soft, whereas the homogenate particles were tough.

A batch of essentially undisrupted cells of Arthrobacter B 3726 was treated in the same way, but proved impossible to immobilize in a satisfactory way, as no stable shaped bodies could be produced.

EXAMPLE X

Comparison between different degrees of cell disruption.

A concentrate $a$ (50% disruption) was prepared as in Example 6 and half of it, $b$ (90% disruption), as in Example 6.

200 ml of each were then mixed for 20' with 8 ml 50% w/w glutaraldehyde, frozen, thawed at 20°C., and the gel thus formed were squeezed, broken up, agitated 20' in 1 liter deionized water, filtered, pressed on the filter, redispersed in 1 liter deionized water, refiltered, dried at 20°C., and granulated. 5 g of each were tested with the 40% w/w glucose at 30 ml/hour, to show the following performance after 20 hours:

|     | % conversion |
| --- | --- |
| (a) | 40.9 |
| (b) | 45.1 |

When checked for rigidity after the run, $a$ was found to be soft, whereas $b$ was tough.

EXAMPLE XI

Glutaraldehyde requirement, concentrate and homogenate.

Granules were prepared from concentrate (55% disruption) and from homogenate (96% disruption) as in Example 10 only with different glutaraldehyde concentrations, agitated for 20 hours in deionized $H_2O$ at 60°C., and checked for rigidity according to the following method: the particles are pressed as hard as possible between two fingers and the following scale noticed:

| Scale | Details |
| --- | --- |
| 1 | completely "pasted" |
| 2 | "pasted" to a substantial degree |
| 3 | "pasted" to a small degree only |
| 4 | no "pasting", tough |
| 5 | very tough |
| 6 | extremely tough |

The minimum rigidity believed to be suitable for industrial use is considered to be 3 or 4.

The above granules gave the following results:

| % glutaraldehyde | rigidity scale | |
| --- | --- | --- |
|  | concentrate | homogenate |
| 1.0 | * | 2–3 |
| 1.5 | 1 | 4 |
| 2.0 | 2 | 5 |
| 2.5 | 3–4 | 6 |

*too soft to granulate

EXAMPLE XII

Effect of thawing.

An unhomogenized concentrate as in Example 7 without the drying step was divided in two: One half was stirred at 3°C. with 10 ml 20% w/w glutaraldehyde per 100 ml of concentrate, pH 6.8 for 2 minutes, frozen in an ethanol/dry ice bath, left to thaw at 20°C., dispersed in deionized water, pressed on the filter and dried at 20°C. The other half was treated in the same way, only it was not thawed but freeze-dried instead. 5 g particles of each process were then tested as in Example 6 at 30 ml/hour, with the following results after 20 hours:

| Process | % conversion |
| --- | --- |
| a) freezing, thawing | 37.8 |
| b) freeze-drying | 35.6 |

A homogenized concentrate (200 ml) treated in the same fashion, then frozen and thawed produced 19.1 g of tough particles which tested out to a 42.4% conversion of 40% w/w glucose syrup after 20 hours at a feed rate of 24 ml/hour.

EXAMPLE XIII

Freezing circumstances.

A homogenized concentrate glutaraldehyde reacted as in Example 12 was frozen in an ethanol/dry ice bath with stirring. then thawed. The particles obtained were similar to the comparable homogenate particles made according to Example 12.

A like preparation was frozen by adding dry ice to the cross-linking mixture. The mixture froze in just a few minutes. The particles obtained were less fibrous, more porous.

What is claimed:

1. A method for production of an enzymatically active physically stable water insoluble glucose isomerase product from microorganism cells exhibiting glucose isomerase activity which comprises:
   a. concentrating and homogenizing the microorganism cells into a homogenized cell concentrate containing ruptured cells and having a dry matter content containing from 3–30% weight by volume;
   b. reacting said cell concentrate with from 0.01–1.0 parts by weight of glutaraldehyde per part of dry matter content to form thereby a coherent solid product; and
   c. thereafter removing water and shaping the coherent product into a subdivided form.

2. The process of claim 1 wherein the glutaraldehyde is from 0.05–0.3 parts.

3. The process of claim 1 wherein water is removed from the coherent product in step (c) by drying to at least 80% by weight dry matter content.

4. The process of claim 1 wherein (c) constitutes water washing and granulating the coherent product, then drying to a dry matter content of at least 80% by weight.

5. The process of claim 1 wherein the cell concentrate is subjected to flocculation after homogenization.

6. The process of claim 1 wherein step (b) comprises admixing glutaraldehyde and the cell concentrate to form thereby a reaction mixture and freezing then thawing said reaction mixture.

7. The process of claim 1 wherein step (c) comprises extrusion of the product followed by drying of the extruded product.

8. The process of claim 5 wherein in step (c) the coherent product of the glutaraldehyde -cell concentrate reaction is washed, filtered and granulated to remove water and shape the product.

9. The process of claim 8 wherein the granulated product is dried to a dry matter content at least 80% by weight.

10. The process of claim 6 wherein step (c) comprises washing then dewatering, to remove water from the coherent product.

11. The process of claim 10 wherein the dewatered product is dried to a dry matter content of at least 80% by weight.

* * * * *